US008547090B2

(12) United States Patent
Lukin et al.

(10) Patent No.: US 8,547,090 B2
(45) Date of Patent: Oct. 1, 2013

(54) ELECTRONIC SPIN BASED ENHANCEMENT OF MAGNETOMETER SENSITIVITY

(75) Inventors: Mikhail D. Lukin, Cambridge, MA (US); Ronald L. Walsworth, Cambridge, MA (US); Amir Yacoby, Cambridge, MA (US); Paola Cappellaro, Cambridge, MA (US); Jacob M. Taylor, Cambridge, MA (US); Liang Jiang, Cambridge, MA (US); Lilian Childress, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 314 days.

(21) Appl. No.: 12/746,128

(22) PCT Filed: Dec. 3, 2008

(86) PCT No.: PCT/US2008/085428
§ 371 (c)(1),
(2), (4) Date: Aug. 24, 2010

(87) PCT Pub. No.: WO2009/073740
PCT Pub. Date: Jun. 11, 2009

(65) Prior Publication Data
US 2010/0315079 A1    Dec. 16, 2010

Related U.S. Application Data

(60) Provisional application No. 60/991,872, filed on Dec. 3, 2007, provisional application No. 61/058,366, filed on Jun. 3, 2008.

(51) Int. Cl.
*G01R 33/02* (2006.01)

(52) U.S. Cl.
USPC ...................................................... 324/244.1

(58) Field of Classification Search
USPC ...................................................... 324/244.1
See application file for complete search history.

(56) References Cited

U.S. PATENT DOCUMENTS 3,150,313 A * 9/1964 Dehmelt ..................... 324/304
3,701,005 A * 10/1972 Hartline ..................... 324/301
(Continued)

OTHER PUBLICATIONS

Osipov et al. Paramagnetic defects and exchange coupled spins in pristine ultrananocrystalline diamonds, Jun. 23, 2007, pp. 2025-2038.*

(Continued)

*Primary Examiner* — Jermele M Hollington
*Assistant Examiner* — Demetrius Pretlow
(74) *Attorney, Agent, or Firm* — Wilmer Cutler Pickering Hale and Dorr LLP

(57) ABSTRACT

A method is disclosed for increasing the sensitivity of a solid state electronic spin based magnetometer that makes use of individual electronic spins or ensembles of electronic spins in a solid-state lattice, for example NV centers in a diamond lattice. The electronic spins may be configured to undergo a Zeeman shift in energy level when photons of light are applied to the electronic spins followed by pulses of an RF field that is substantially transverse to the magnetic field being detected. The method may include coherently controlling the electronic spins by applying to the electronic spins a sequence of RF pulses that dynamically decouple the electronic spins from mutual spin-spin interactions and from interactions with the lattice. The sequence of RF pulses may be a Hahn spin-echo sequence, a Can Purcell Meiboom Gill sequence, or a MREV8 pulse sequence, by way of example.

17 Claims, 9 Drawing Sheets

(56) References Cited

U.S. PATENT DOCUMENTS

| | | | | |
|---|---|---|---|---|
| 4,005,355 | A | * | 1/1977 | Happer et al. ............... 324/304 |
| 4,063,158 | A | * | 12/1977 | Sabisky et al. ............... 324/224 |
| 4,193,029 | A | * | 3/1980 | Cioccio et al. ............... 324/301 |
| 4,560,867 | A | * | 12/1985 | Papuchon et al. ............. 250/225 |
| 4,806,864 | A | * | 2/1989 | Schearer et al. .............. 324/301 |
| 5,036,278 | A | * | 7/1991 | Slocum ........................ 324/304 |
| 5,168,224 | A | * | 12/1992 | Maruizumi et al. .......... 324/300 |
| 5,227,725 | A | * | 7/1993 | Cory et al. .................... 324/309 |
| 5,321,258 | A | * | 6/1994 | Kinney ..................... 250/227.21 |
| 5,534,776 | A | * | 7/1996 | Leger et al. ................... 324/304 |
| 5,623,205 | A | | 4/1997 | Tomita et al. |
| 6,100,687 | A | * | 8/2000 | Weitekamp et al. .......... 324/300 |
| 6,437,413 | B1 | * | 8/2002 | Yamaguchi et al. .......... 257/421 |
| 6,472,869 | B1 | * | 10/2002 | Upschulte et al. ............ 324/304 |
| 6,788,051 | B2 | * | 9/2004 | Blais ........................ 324/244.1 |
| 6,930,479 | B2 | | 8/2005 | Xiao et al. |
| 7,038,458 | B1 | | 5/2006 | Wiegert |
| 7,042,213 | B2 | | 5/2006 | Greywall |
| 7,046,002 | B1 | | 5/2006 | Edelstein |
| 7,053,610 | B2 | * | 5/2006 | Clarke et al. ................. 324/300 |
| 7,084,624 | B2 | | 8/2006 | Tokura et al. |
| 7,199,584 | B2 | * | 4/2007 | Meriles ........................ 324/316 |
| 7,474,095 | B2 | * | 1/2009 | Levitt et al. ................... 324/300 |
| 7,573,264 | B2 | * | 8/2009 | Xu et al. ....................... 324/304 |
| 2003/0016013 | A1 | * | 1/2003 | Kruspe et al. ................. 324/303 |
| 2003/0137297 | A1 | * | 7/2003 | Ganesan ....................... 324/303 |
| 2004/0012388 | A1 | * | 1/2004 | Pedersen .................... 324/244.1 |
| 2004/0196037 | A1 | * | 10/2004 | Xiang et al. .................. 324/300 |
| 2005/0088248 | A1 | * | 4/2005 | White .......................... 331/94.1 |
| 2007/0153254 | A1 | * | 7/2007 | Huang et al. ................ 356/4.01 |
| 2010/0308813 | A1 | | 12/2010 | Lukin et al. |

OTHER PUBLICATIONS

"Written Opinion of the International Searching Authority" for PCT/US2008/085428, International Searching Authority/European Patent Office, Munich,Germany.

"International Search Report" for PCT/US2008/085428, International Searching Authority/European Patent Office, Munich, Germany.

Taylor, et al., "High-Sensitivity Diamond Magnetometer With Nanoscale Resolution" May 9, 2008.

Hanson R. et al., "Coherent Dynamics of a Single Spin Interacting with an Adjustable Spin Bath," Science, American Association for the Advancement of Science USA, vol. 320, No. 5874, pp. 352-355, Apr. 18, 2008.

Pieter Kok et al., Qubits in the Pink, Nature, vol. 444, No. 2, Nov. 1, 2006, pp. 49-49, XP002525798.

Epstein et al., Anisotropic Interactions of a Single Spin and Dark-spin Spectroscopy in Diamond, Nature Physics, vol. 1, Nov. 2005, 18 pages.

Hanson et al., "Room-Temperature Manipulation and Decoherence of a Single Spin in Diamond," Quantum Physics, Phys. Rev. B 74, 2006, pp. 087601-1 to 087601-4, 6 pages.

Lilliam Isabel Childress, "Coherent Manipulation of Single Quantum Systems in the Solid State," Physics, Harvard University, Cambridge, Massachusetts, Mar. 2007, 188 pages.

Rabeau, et al., Single Nitrogent Vacancy Centers in Chemical Vapor Deposited Diamond Nanocrystals, Nano Letters, 2007, vol. 7, No. 11, 8 pages.

* cited by examiner

ELECTRONIC SPIN BASED ENHANCEMENT OF MAGNETOMETER SENSITIVITY

CROSS-REFERENCE TO RELATED APPLICATIONS

This application is based upon, and claims the benefit of priority under 35 U.S.C. §119(e) from U.S. Provisional Patent Application Ser. No. 60/991,872 (the "872 provisional application"), filed Dec. 3, 2007, entitled "High Sensitivity Solid State Magnetometer"; and from U.S. Provisional Patent Application Ser. No. 61/058,366 (the "366 provisional application"), filed Jun. 3, 2008, entitled "High Sensitivity Solid State Magnetometer." The contents of the '872 provisional application and the '366 provisional application are incorporated herein by reference in their entireties as though fully set forth.

This application is related to PCT Application No. PCT/US08/85424, filed concurrently herewith on Dec. 3, 2008, entitled "High Sensitivity Solid State Magnetometer," the content of which is incorporated herein by reference in its entirety.

BACKGROUND

The detection of weak magnetic fields with high spatial resolution is an important problem in diverse areas ranging from fundamental physics and material science to data storage and biomedical science.

Over the past few decades, a wide variety of magnetic sensors have been developed using approaches that include, but are not limited to, SQUIDs (superconducting quantum interference devices), atomic vapor-based magnetometers, and magnetic resonance force microscopy. Even state-of-the-art systems have great difficulty, however, in detecting weak magnetic fields in small regions of space and under ambient environmental conditions such as temperature.

Magnetometers based on solid state electronic spin systems have been proposed in co-pending PCT application No. PCT/US08/85424, filed concurrently herewith on Dec. 3, 2008, the contents of which are incorporated herein by reference. One of the advantages of such solid state spin systems is that they have the potential to achieve a very high density of sensing spins, which in turn translates into an improvement of sensitivity to the average magnetic field over the magnetometer volume.

At very high spin densities, however, couplings among the electronic spins may no longer be ignored. The electronic spins may lose spin coherence by interacting with mutually resonant photon frequencies, causing the electronic spins to flip by energy transfer, through mutual spin-orbit coupling, and through photon emission.

It is desirable to provide methods and systems for increasing the sensitivity of magnetometers that are based on solid state electronic spin systems. At high spin densities, in particular, methods and systems for decoupling electronic spins from each other and from the local environment are needed.

SUMMARY

A method is disclosed for increasing the sensitivity of a solid state electronic spin based magnetometer that makes use of individual electronic spins or ensembles of electronic spins in a solid-state lattice. The method involves coherently controlling the electronic spins by applying to the electronic spins a sequence of RF pulses that dynamically decouple the electronic spins from mutual spin-spin interactions and from interactions with the lattice. In some embodiments, the sequence of RF pulses may be a Hahn spin-echo sequence, or a Carr Purcell Meiboom Gill sequence, or a MREV8 pulse sequence.

BRIEF DESCRIPTION OF DRAWINGS

The drawing figures depict one or more implementations in accord with the present concepts, by way of example only, not by way of limitations. The drawings disclose illustrative embodiments. They do not set forth all embodiments. Other embodiments may be used in addition or instead. In the figures, like reference numerals refer to the same or similar elements.

DETAILED DESCRIPTION

In the present disclosure, methods and systems are described for using solid-state electronic spin systems, including but not limited to defects in crystals and semiconductors, for precision sensing of weak magnetic fields and magnetic fields in small volumes. It is shown that solid state systems containing electronic spins can be used as high sensitivity magnetometers by manipulating the electronic spins and probing their behaviors with light and with RF (radiofrequency) electromagnetic fields. Nanometer-scale spatial resolution together with high magnetic field sensitivity can be obtained by probing a single electronic spin system. By probing a plurality of electronic spins (typically an ensemble of electronic spins), at a relatively high density, the sensitivity to magnetic fields may be substantially increased, even though spatial sensitivity may decrease somewhat. Augmentation with optical imaging techniques (e.g., using CCD arrays) can allow imaging of magnetic field spatial patterns. Integration with AFM (atomic force microscopy), magnetic field gradients, super-resolution (e.g., STED (stimulated emission depletion) microscopy) or other techniques can allow magnetic field patterns to be imaged with spatial resolution better than the conventional optical diffraction limit, at a scale near or better than ten nanometers NV centers in the diamond lattice is one example of such solid state electronic spin systems, which are atom-like. As described below, these electronic spin systems can be used to detect magnetic fields with unprecedentedly high sensitivity, as well as to detect the variation in the magnetic field with very high spatial resolution.

Figure 1:
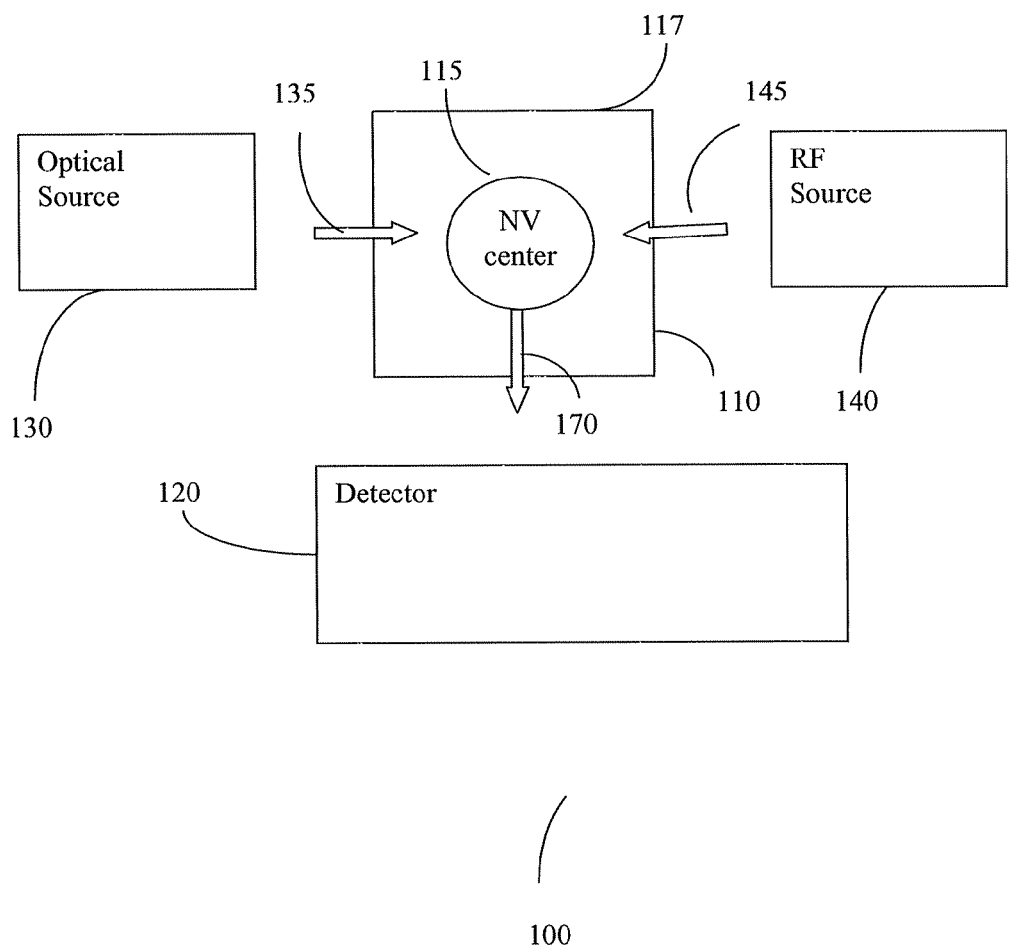
FIG. 1 is a schematic block diagram of a solid state magnetometer including a single NV center, in accordance with one embodiment of the present disclosure.

FIG. 1 is a schematic block diagram of a high sensitivity solid state magnetometer 100 based on a NV center in diamond, in accordance with one embodiment of the present disclosure. In overview, the solid state magnetometer 100 includes an electronic spin system 110 that includes at least one Nitrogen vacancy 115 in a carbon lattice 117 of diamond; and a detector 120 configured to detect the Zeeman shift in the energy level of the electronic spin system 110 in response to light 135 and an RF excitation field 145 applied thereto. The magnetometer 100 may further include an optical source 130 and an RF field generator 140.

A NV center in diamond is a crystallographic defect in the structure of a diamond, i.e., an empty position in a diamond's lattice. The vacancies may interact with interstitial atoms, such as Nitrogen, and may act as color centers by absorbing visible light. The NV center is found as a defect in the lattice structure of a single crystal diamond. The NV impurity is based in the lattice of carbon atoms, where two adjacent sites are altered, because one carbon atom is replaced with a Nitrogen atom and the other space is left vacant. NV centers are visible as red spots when illuminated by laser.

The NV center is relatively insulated from magnetic interference from other spins. The quantum state of the spin of the NV center may be probed controlled at room temperature. NV centers in diamond, as well as systems involving other types of defects in regular solid state lattices, may provide electronic spins that have almost no interaction with the background lattice, i.e., nearly pure electronic spins that are practically frozen in space, with almost no corrupting interactions with the background lattice. Such electronic spins, which are practically motionless in free space, may be optically detectable with unique optical signatures that allow them to be used for magnetometry.

In the illustrated embodiment, the NV center 115 is an idealized electronic spin, as described above. The NV center 115 is configured to receive optical radiation 135 from the optical source 130, and to align itself with the magnetic field in response to the optical radiation 135.

The optical source 130 may be configured to generate light 135 which, when applied to the electronic spin system, i.e., the NV center 115, causes the electronic spin to align along one or more well-defined directions. For example, the optical source 130 may be a laser. In one embodiment, the laser may generate light 135 that has a wavelength of about 520 nm and has green color.

An external perturbation, for example an ESR (electron spin resonance) field 145 or pulses of RF radiation that are applied to the electronic spin or NV center 115 may cause the electronic spin 115 to precess. The external perturbation may cause a detectable splitting in the electronic spin energy levels, i.e. may cause a detectable Zeeman shift that is proportional to the magnetic field being measured. In the embodiment illustrated in FIG. 1, an RF source 140 may generate an RF field, or pulses of RF radiation.

In the present application, the terms "ESR field", "RF field," and "RF radiation" have the same meaning, and are used interchangeably.

The magnetometer 100 operates by detecting the accumulated phase resulting from the relative energy shift induced by a magnetic field b between two Zeeman sublevels, $$\delta\omega \propto \frac{g\mu_B}{\hbar} b.$$

This allows for the precise estimation of an applied DC or AC magnetic field b. The ultimate sensitivity of such sensors is determined by the linewidth of the spin transition and by the signal-to-noise ratio.

A detector 120 detects output optical radiation from the NV center 115 after the light 135 from the laser 130 and the RF or ESR field 145 have passed therethrough. In some embodiments, the detector may be configured to create an image of the optical radiation emitted from electronic spins in different regions of the solid-state system, thereby allowing the magnetic field to be imaged. The detector may also employ super-resolution (for example, STED), atomic force microscopy, magnetic field gradients or other techniques to provide location of the electronic spin or spins (and hence the magnetic field) better than the conventional optical diffraction limit. The detector 120 thus may include, but is not limited to, combinations of CCD (charge coupled device) arrays, confocal microscopy, super-resolution optical techniques (e.g., STED), optical fibers, plasmonic waveguides, atomic force microscopy, and magnetic field gradients. A control and data processing system, which may be integrated with the detector 120, may determine the magnitude of the Zeeman shift and thus calculate the magnetic field, from the detected output radiation from the NV center 115.

Figure 2:
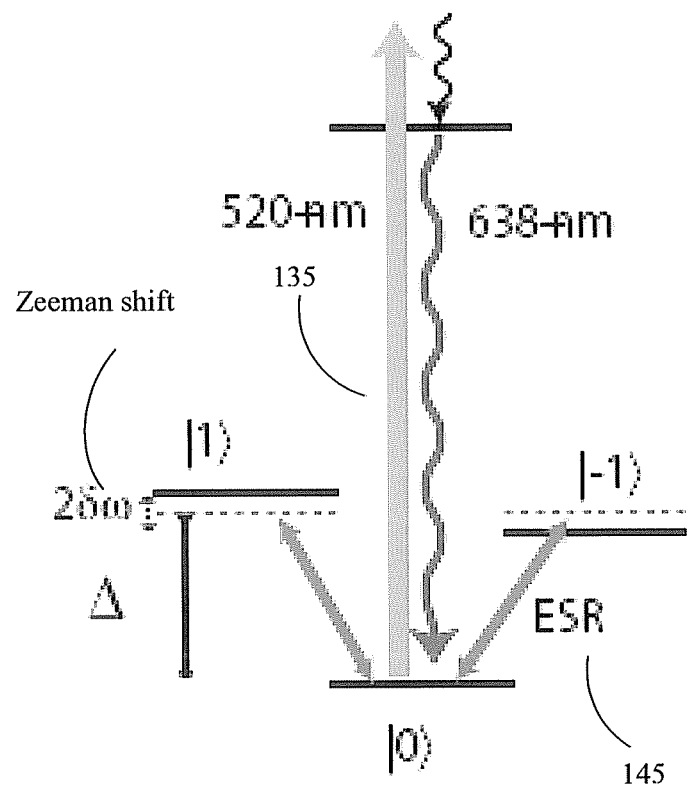
FIG. 2 illustrates the energy level structure of a single NV center.
Figure 3:
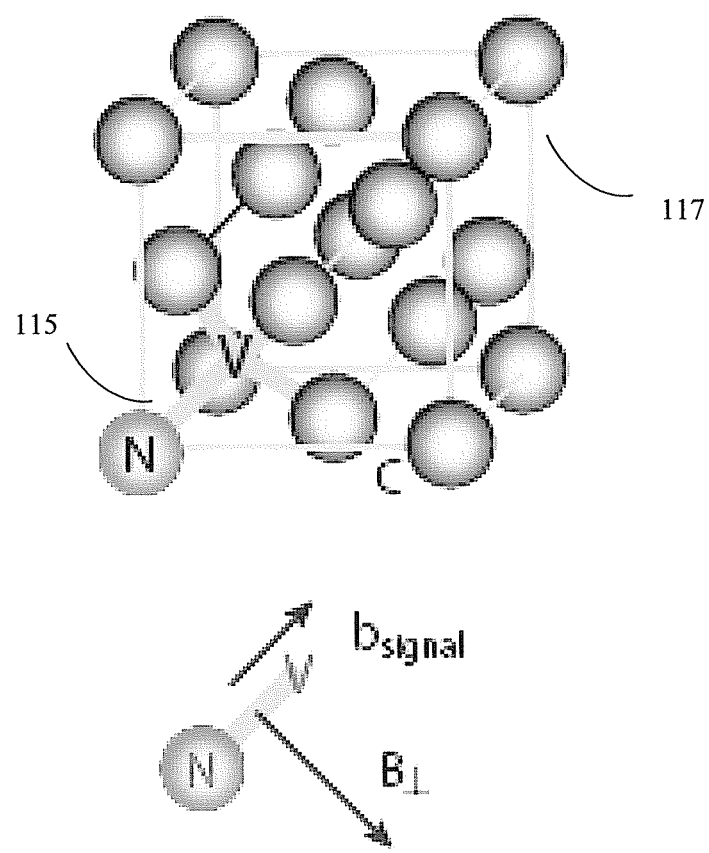
FIG. 3 illustrates the crystal structure of diamond with a (111) NV center.
Figure 4:
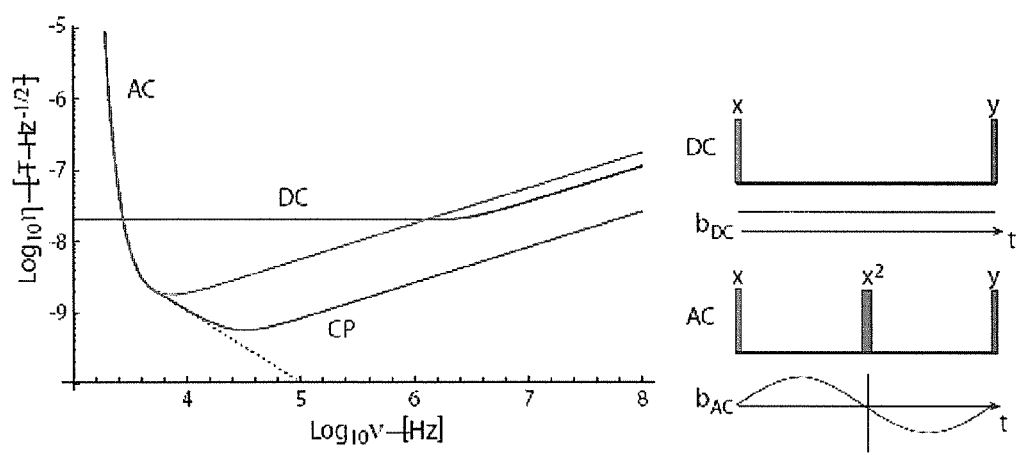
FIG. 4 illustrates the DC (direct current) and AC (alternating current) sensitivity to magnetic fields for a single NV center as a function of signal frequency.

FIGS. 2-4 illustrate further details of magnetometry in accordance with the embodiment illustrated in FIG. 1, namely an embodiment in which magnetometers are used that contain at least one Nitrogen-vacancy center(s) in diamond.

FIG. 2 illustrates the level structure of a single NV center. As shown in FIG. 2, the fine structure of the electronic ground state of a NV center is a spin triplet (having |1>, |0>, and |−1> states), with a $\Delta = 2.88$ GHz crystal field splitting and a Zeeman shift $\delta\omega$. As indicated in FIG. 2, under the application of excitation light 135 having a wavelength of about ~530 nm, the NV center exhibits SDPL (spin-dependent photo-luminescence) near the zero phonon line at about 638 nm, even at room temperature. This allows for optical detection of ESR and optical pumping of the spin state of the NV center, as well as allowing phase shifts resulting from the magnetic field to be sensed: the excitation light helps put the spins into the |1>, |0>, or |−1> states, in varying proportions.

The crystal field splits the $m_s = \pm 1$ sub-levels from the $m_s = 0$ sub-level by $\Delta = 2\pi \times 2.88$ GHz, allowing resonance techniques at vanishing external field. At low field, $\Delta$ is the highest energy scale and sets the quantization axis to be parallel to the Nitrogen-to-vacancy direction.

The secular Hamiltonian, including a small external field, $\vec{B}(t) = (B_x, B_y, B_z)$, is $$H = \hbar \Delta S_z^2 + g\mu_B B_z S_z$$

where $B_z$ is the component of the magnetic field along the NV center's axis and $S_z$ takes the values $m_s = 0, \pm 1$. Terms proportional to the perpendicular field are suppressed to order $B_{x,y}^2/\Delta$, and may be neglected.

By using the $m_s = \pm 1$ manifold in a low external magnetic field, the NV center acts as a vector magnetometer, sensitive only to fields aligned with its quantization axis. This manifold is twice as sensitive to the signal field than the 0-1 manifold, can operate with high-power microwave ESR fields even at vanishing external magnetic fields, and is insensitive to phase errors in the microwave source. Furthermore, the ±1 manifold is less affected by nuclear spin-induced decoherence at low fields, since inter-nuclei interactions are effectively quenched by the large hyperfine field and dephasing can be refocused by spin echo.

FIG. 3 illustrates the crystal structure of a diamond lattice 117 having a (111) NV center 115. As seen in FIG. 3, there are four crystallographic classes of centers, each oriented along a different (111) axis. For this reason, a transverse (DC) magnetic field $B_\perp \geq 0.3$ mT must be applied to detune the other three classes. Thus, the ESR field used for quantum control only affects the class whose crystalline axis is aligned with the external magnetic field.

In one embodiment of the present disclosure, coherent control of the NV center's states may be obtained via an ESR magnetic field, oscillating at the angular frequency $\Delta$. In some embodiments, a variety of ESR control techniques may be implemented. It is known that the NV center's spin triplet is an inverted lambda system. An external linearly polarized microwave magnetic field tuned to the crystal field splitting drives transitions between $|0\rangle$ and the superposition $|+\rangle = (|1\rangle + |-1\rangle)/\sqrt{2}$, while the state $|-\rangle = (|1\rangle - |-1\rangle)/\sqrt{2}$ is dark—it is decoupled from the field due to destructive interference.

Application of a small magnetic field aligned with the NV center z axis breaks this interference effect, and allows for complete quantum control of the spin triplet manifold. An echo sequence would have the traditional $\pi/2$-$\pi$-$\pi/2$ structure replaced by $\pi$-$2\pi$-$\pi$: the first pulse creates $|+\rangle$, the second induces a relative $\pi$-phase between $|+\rangle$ and $|-\rangle$, and the third converts $|+\rangle$ to $|0\rangle$ while leaving $|-\rangle$ population trapped in the $m_s = \pm 1$ manifold.

Linearly polarized ESR pulses may rotate between the two dimensional sub-space of $|0\rangle$ and $|+\rangle = (|1\rangle + |-1\rangle)/\sqrt{2}$. Additional phase control may be provided by a background oscillating reference field $\lfloor B_{ref} \sin(2\pi/\tau) \rfloor$ along the z-axis. In one embodiment, choosing $B_{ref} = (\hbar/g\mu_B)\pi^2/8\tau$ may yield an optimal phase offset to achieve a signal linear in the field strength.

FIG. 4 illustrates the sensitivity as a function of the signal frequency for both AC and DC detection, for the case of a single NV center. For diamond with natural abundance of C-13 nuclei, $T_2^* \approx 1$ μs and $T_2 \approx 0.3$ ms, sensitivities of about $\eta_{DC} \approx 200$ nT Hz$^{-1/2}$ and $\eta_{AC} \approx 10$ nT Hz$^{-1/2}$ may be obtained for a single NV center with this approach.

In one embodiment of the present disclosure, a typical approach to the measurement of magnetic fields may be adopted, in which a Ramsey-type decoupling sequence is used, as illustrated in the right hand side of FIG. 4. As shown in FIG. 4, a $\pi/2$-pulse creates a superposition of two Zeeman levels, which acquire a relative phase $$\phi = \delta\omega_\tau \propto \frac{g\mu_B}{\hbar} b$$

due to the external field b during the free evolution interval $\tau$, where $\mu_B$ is the Bohr magneton and g is about $\approx 2$ for NV centers. Another $\pi/2$-pulse transforms the phase into a population difference, from which the Zeeman shift is inferred by SDPL. For small $\phi$, the signal depends linearly on the field:

$$S \approx \frac{g\mu_B}{\hbar} b\tau.$$

In the embodiment illustrated in FIG. 4, the following relaxation and measurement times, appropriate for the case of NV centers where the bath is constituted by the 1.1% natural abundant Carbon-13 spins, were used: $T_2^* = 1$ μs[6], T2=250 μs[7], and $t_M = 1$ μs. In addition, a measurement efficiency parameter C was set to C=0.5.

Higher frequency signals may be measured using composite pulse sequences, which include but are not limited to CP (Carr-Purcell) sequences, with an improvement in sensitivity. Ideally, the sensitivity could improve indefinitely at higher frequencies by increasing the number of pulses, as seen by the dotted line. In practice, pulse errors will eventually, reduce the achievable sensitivity, as shown by the solid line. A pulse error probability of 0.002 was used in the illustrated embodiment.

The control sequences illustrated in the top right hand side of FIG. 4 is the DC pulse sequence. Starting with a polarized spin, an initial $\pi/2$ pulse about the x axis is shown as rotating the spin to the y axis, where it can precess for a free evolution interval $\tau$. This free evolution leads to a phase rotation about the z axis by an amount $\phi = \delta\omega\tau$. A final $\pi/2$ pulse about the y axis is shown as rotating the x component of the spin to the z axis, where measurement of the spin reveals oscillations in the z component $\propto \sin(\phi)$.

In the bottom right hand side of FIG. 4, the AC pulse sequence is illustrated, consisting of $\pi/2|_x$-$\pi|_x$-$\pi/2|_y$. For small accumulated phases, a signal linear in the field can also be obtained with all the pulses along the x direction if a reference field $B_{ref}\sin(2\pi/\tau)$ is added. The measurement of the population in the $|0\rangle$ state at the end of the sequence yields $P = \frac{1}{2}[1+\cos(\delta\phi)]$, where $$\delta\phi_{22} = \frac{g\mu_B}{\hbar/\tau}[4B_{ref}/\pi + bf(\nu\tau, \phi)].$$

The reference field provides an offset of the cosine function to its point of maximal slope at $$B_{ref} = \frac{\pi^2 \hbar}{8g\mu_B\tau}$$

resulting in $$P - 1/2 \approx \frac{g\mu_B\tau}{\hbar} bf(\nu\tau, \phi)\bigg].$$

Increasing $\tau$ improves the sensitivity until random perturbations, such as environmental perturbations, lead to decoherence and the accompanying decay of the free-precession signal. A principle difference between isolated atomic systems and solid-state electronic spins is that the latter couple strongly to their environment, resulting in relatively short coherence times and a correspondingly short $\tau$. In the case of electronic spin systems, the coherence is limited by interactions with lattice nuclei, resulting in an ensemble dephasing time $T^*_2$. Furthermore, the measurement efficiency, denoted by C, may be less than unity, as further described below. Thus the sensitivity of a magnetometer based a single electronic spin is given by $$\eta_{DC} \approx \frac{\hbar}{g\mu_B C\sqrt{T_2^*}}.$$

The sensitivity of the magnetometer may be improved for AC fields with coherent control techniques. Due to the long correlation times of the lattice nuclei, a spin echo may dramatically extend the relevant coherence times. This approach, illustrated in FIG. 4, is a Hahn-echo sequence, in which the Ramsey free evolution is interrupted by an additional microwave π pulse at τ/2. The resulting averaged evolution removes slowly varying fields. At the same time, a signal field b(t) oscillating in-phase with the pulse sequence produces an additive phase shift. The phase accumulated in the two time intervals is $$\delta\phi = \frac{g\mu_B}{\hbar}\left[\int_0^{\tau/2} b(t)dt - \int_{\tau/2}^{\tau} b(t)dt\right].$$

For a signal field $$b(t) = b\sin(vt + l_0), \delta\phi = \frac{g\mu_B}{\hbar}b\tau f(vt + l_0),$$

with $$f(x, l_0) = \frac{\sin^2(x/4\cos(x/2 + l_0)}{x/4}.$$

For maximal response to CW signals (assuming small b), τ=2π/v and $l_0$=0 were found to be optimal. In essence, the spin echo allows the limit associated with $T^*_2$ to be extended to an intrinsic dephasing time $T^*_2$, at the cost of a reduced bandwidth and insensitivity to frequencies≤1/$T_2$. For a bath of dipolar-coupled spins, the signal is expected to decay as exp[$-((\tau/T_2)^3)$], and the sensitivity is improved by $\sqrt{T^*_2/T_2}$:

$$\eta_{AC} \approx \frac{\pi\hbar}{2g\mu_B C\sqrt{T_2}}.$$

It is possible to further improve the sensitivity for higher-frequency signals, since the interrogation time need not be limited by the period of the oscillation but can be multiples of it. By using a sequence of $2\eta_c$ π-pulses, the interrogation time can be extended to $2\pi n_c/v \approx T_{CP}$, where $T_{CP}$ is the effective decay time under the pulse sequence. This decay time is usually longer than $T_2$: for example, $T_{CP} \sim n_c^{2/3} T_2$ for a Lorentzian noise spectrum. This results in further enhancement of sensitivity that is, in principle, limited only by errors associated with refocusing pulses.

Figure 5:
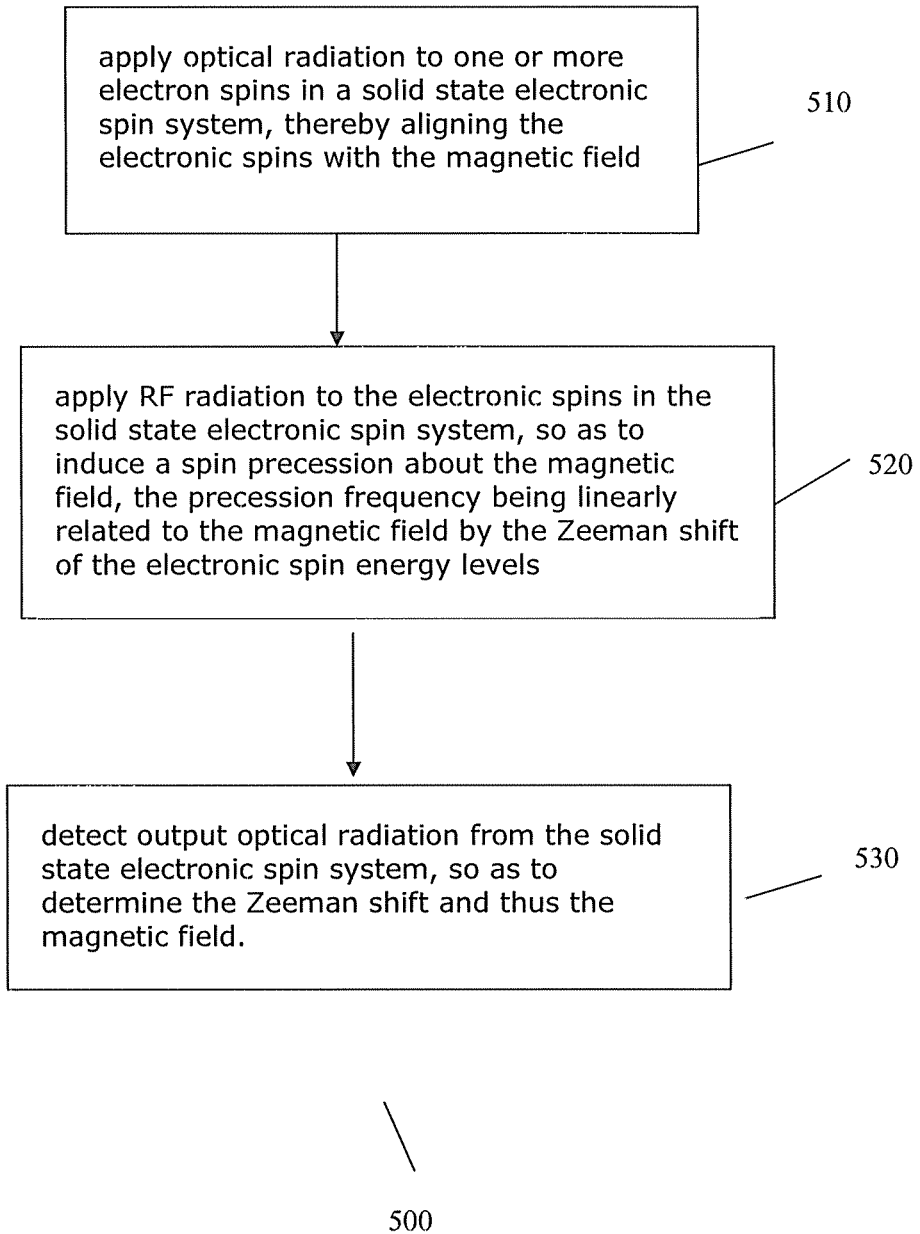
FIG. 5 is a schematic flow chart of a method of detecting a magnetic field, in one embodiment of the present disclosure.

FIG. 5 is a schematic flow chart of a method 500 of detecting a magnetic field, in one embodiment of the present disclosure. In operation, the method 500 may include an act 510 of applying optical radiation to a solid state electronic spin system that contains at least one electronic spin within a solid state lattice, thereby aligning the electronic spin with the magnetic field. The method 500 may further include an act 520 of applying one or more pulses of RF radiation to the solid state electronic spin system so as to rotate the electronic spins and cause a Zeeman shift in the electronic spin energy level, proportional to the magnetic field.

The method 500 may further include an act 530 of detecting output radiation from the solid state electronic spin system after the optical excitation radiation and the RF radiation have passed through the electronic spins in the solid state electronic spin system, so as to determine the Zeeman shift and the magnetic field from the output radiation.

Several approaches may be envisioned for implementing magnetic sensors using the above-described methods and systems. For example, a diamond nano-sized crystal containing one or several NV centers can be attached to a tip of a tapered fiber, an atomic force microscope, or a plasmonic waveguide. This may be used as a scanning magnetic probe, capable of probing localized sources of magnetic fields. Magnetic field gradients may be applied to increase the spatial resolution of the sensor by localizing the region of electron spin resonance with the applied RF radiation. Confocal microscopy and super-resolution optical techniques (such as STED) may be used to image NV centers in diamond nanocrystals with spatial resolution better than the conventional diffraction limit.

Figure 6:
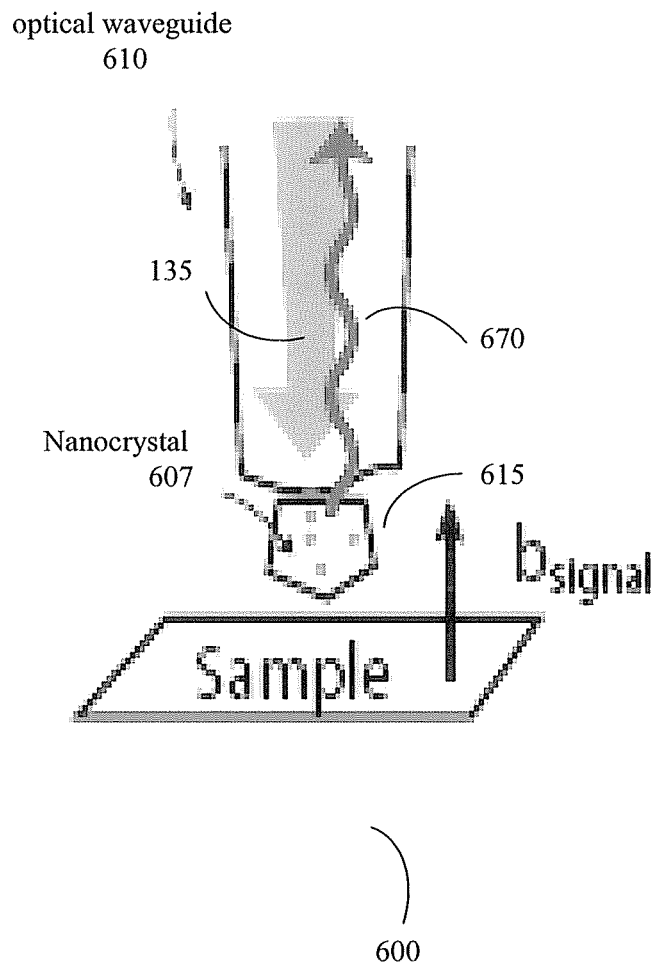
FIG. 6 is a schematic diagram of a magnetometer for probing and measuring localized sources of magnetic fields, including a nano-crystal of diamond attached to end of an optical waveguide, in accordance with one embodiment of the present disclosure.

FIG. 6 is a schematic diagram of a magnetometer 600 for probing and measuring localized sources of magnetic fields, in accordance with one embodiment of the present disclosure. In the embodiment illustrated in FIG. 6, the magnetometer 600 may include a nano-crystal of diamond 607 that is attached at the end of an optical waveguide 610 for photon transmission and collection. The crystal 607 may include a plurality of NV centers 615, each of which acts as a substantially free electronic spin, and each of which is configured to receive optical excitation radiation 135 (optical source not shown for clarity) and RF radiation (not shown for clarity). The optical waveguide 610 may be configured to collect and transmit therethrough photons of the optical radiation and the RF radiation.

Upon receiving the photons of optical radiation that have transmitted through the optical waveguide 610, the electronic spins or NV centers 615 may be configured to align themselves with the magnetic field being sensed. Upon receiving the pulses of RF radiation that have passed through the optical waveguide, the electronic spins 615 may be configured to accumulate a phase resulting from the Zeeman shift induced by the magnetic signal field, which is detected by a detector (not shown) which detects output radiation 670 from the electronic spins 615.

In the embodiment illustrated in FIG. 6, the resolution is limited by the size of the crystal 607. By way of example, a ~25 nm diameter nano-crystal of diamond with about 10 NV centers, attached to the end of an optical fiber or plasmonic waveguide 610 shown and discussed above in conjunction with FIG. 6 would provide sub-100 nm magnetic field resolution while achieving orders of magnitude higher sensitivity than magnetic force microscopy. Provided the waveguide 610 yield high collection efficiency (≈50%), the sensitivity may approach 5 nT Hz$^{-1/2}$, an order of magnitude better than Hall bar- or SQUID-based probes with 10 times better spatial resolution.

This may be particularly important as the field from a magnetic dipole decays as the cube of the distance. Thus, smaller sensors may be brought closer to the source, yielding an improved sensitivity. For example, the magnetic field from a single proton is ~10 nT at 20 nm separation, which an NV nanocrystal magnetometer would be able to detect.

In an augmentation to the embodiment illustrated in FIG. 6, a magnetic field gradient could be applied across the diamond nano-crystal, in order to improve spatial resolution by localizing the spatial region in which the NV center's ESR transition is on resonance with the applied RF radiation. With magnetic field gradients provided by existing technologies, such as nano-scale magnetic tips, this technique would allow spatial localization to <1 nm.

In an alternative embodiment, a bulk diamond sample with a high density of NV centers can be used to sense fields created by extended objects or remote objects, with ultra-high sensitivity.

One principal advantage of using solid-state electronic spins is the potential to achieve extremely high density of sensing spins. This directly translates into an improvement of the sensitivity to the average field over the magnetometer volume, since the shot-noise decreases with increasing electronic spin density n as $1/\sqrt{n}$. Although atomic magnetometers cannot achieve high densities or small volumes without collision-induced reductions in coherence properties, spins in a lattice have fixed locations which allow for substantially higher densities before the deleterious effects of spin-spin interactions impair the magnetometer's operation.

Figure 7:
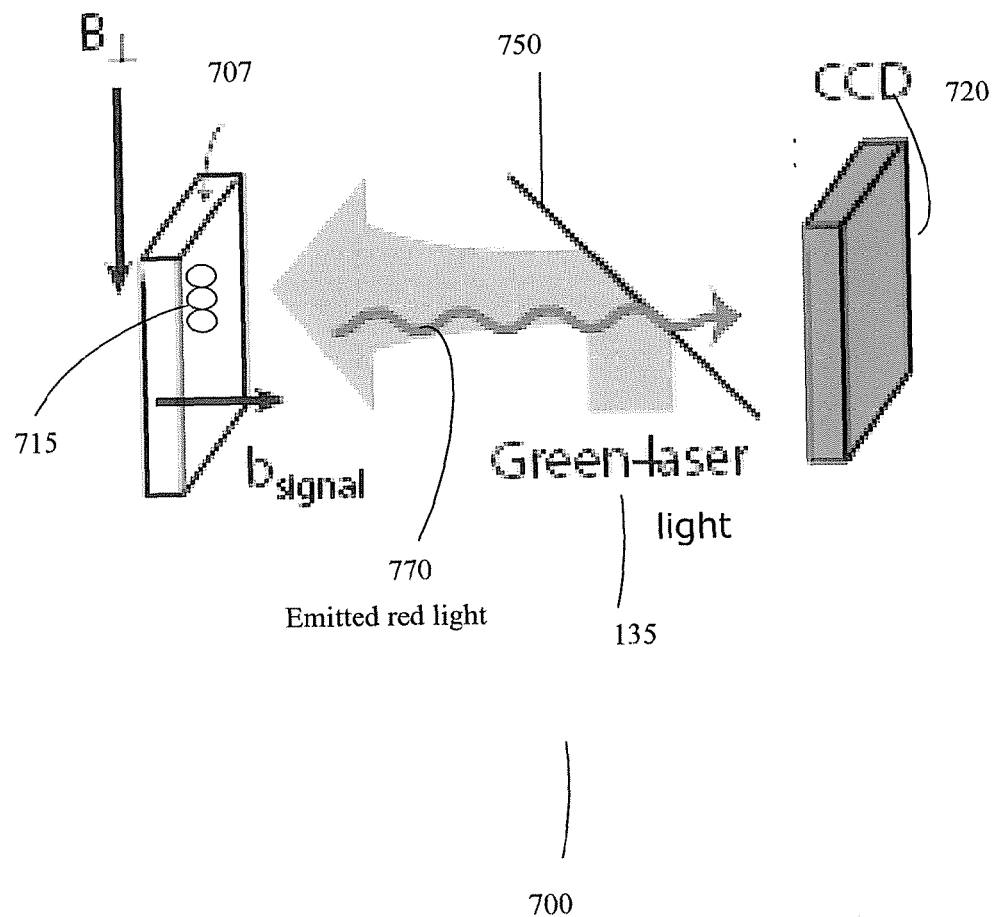
FIG. 7 is a schematic block diagram of a solid state magnetometer including a relatively high density of NV centers within a macroscopic piece of diamond, in accordance with one embodiment of the present disclosure.

FIG. 7 is a schematic block diagram of a solid state magnetometer 700 including a relatively high density of NV centers 715 within a macroscopic piece of diamond 707, in accordance with one embodiment of the present disclosure. In the embodiment illustrated in FIG. 7, the resolution is limited by the wavelength of light. This embodiment allows for very high spatial resolution and signal-to-noise.

In the illustrated embodiment, green laser light 135 produces SDPL, which is detected by measuring red light 770 from the NV centers imaged onto a CCD 720. A dichroic mirror 750 is configured to direct the optical radiation 135 from the laser toward the solid state electronic spin system, i.e. the bulk diamond sample 707, and to direct the output radiation 770 from the solid state electronic spin system 707 toward the CCD 720. The microwave source for spin-resonance is not shown.

In natural diamonds, the density of the desired (negatively charged) NV centers is low (<1 ppm), but it may be artificially increased. To create NV centers in a controlled way, Nitrogen ions may be implanted into diamonds that contain low concentrations of native Nitrogen, followed by annealing to recombine the Nitrogens with vacancies. Assuming a Nitrogen concentration of about 250 ppm with about a 10% conversion, a diamond crystal may be created with a NV center density exceeding about $\sim 10^{18}$ cm$^{-3}$, with an average distance of less than about 10 nm.

At higher densities, the couplings among the electronic spins may no longer be neglected, as they may start to be comparable to $1/T_2$ (4 kHz at 25 nm separation, corresponding to densities $\sim 10^{17}$ cm$^{-3}$). The coupling of a NV center electronic spin to other NV centers ($\vec{S}_k$) and paramagnetic impurities ($\vec{I}_k$, such as Nitrogen) is given by the magnetic dipolar interaction.

To first order in $1/\Delta$ only the terms in the dipolar Hamiltonian commuting with the large crystal-field splitting are effective: $H_{spin\text{-}spin}=H_{zz}+H_{epr}$, with $H_{zz}=\Sigma_{jk}S_{z,j}\vec{D}_{jk}\cdot\hat{z}\hat{S}_{z,k}$ and $H_{epr}=\Sigma_{jk}S_{z,j}\vec{D}_{jk}\cdot\hat{z}\hat{S}_{z,k}$. The dipole interaction vector is $$\vec{D}_{jk} = \frac{\mu_0 g^2 \mu_B^2 [3(\hat{r}_{jk}\cdot\hat{r}_{jk}-\hat{z})]}{4\pi\hbar} \frac{1}{r_{jk}^3},$$

with the $\hat{z}$ axis set by the N-V crystal axis of the sensing spin centers. Spin echo removes, to first order, the effects of the paramagnetic impurities and spectator NV centers (aligned along different crystalline axes), which are out of resonance with the ESR field due to the biasing field $B_\perp$. Additional effects, due to the rapid precession caused by $B_\perp$, lead to a small reduction of the echo envelope, which only causes a slight time- and signal-independent decrease of the spin-echo signal.

However, the interaction $H_{zz}$ between NV centers with the same crystalline axis is unaffected by the spin echo. This interaction results in a decay of the AC magnetometer signal given by $\pi'_k \cos^2(D_{jk}\tau) \approx \exp(-\langle D^2 \rangle \tau^2/2)$ with a dephasing rate averaged over NV center positions $$\sim \sqrt{\langle D^2 \rangle} = \sqrt{\frac{1}{N}\Sigma_{jk}D_{jk}^2}.$$

Since the dipolar interaction is proportional to $1/r^3$, $\langle D^2 \rangle$ scales as the density squared and the sensitivity per root volume $\eta_{AC}^V = \eta_{AC}\sqrt{V}$ is $$\eta_{AC}^V = \frac{\hbar}{g\mu_B} \frac{\pi e^{(\tau/T_2)^3}}{C\sqrt{n\tau}} e^{\alpha n^2 \tau^2},$$

where $\alpha$ is on the order of $$\left(\frac{\mu_0}{4\pi}\frac{(g\mu_B)^2}{\hbar}\right)^2 \approx 1.1 \times 10^{-25} s^{-2} cm^6,$$

and where the fact that the sensing centers are only one fourth of the total NV centers has been taken into account.

Figure 8:
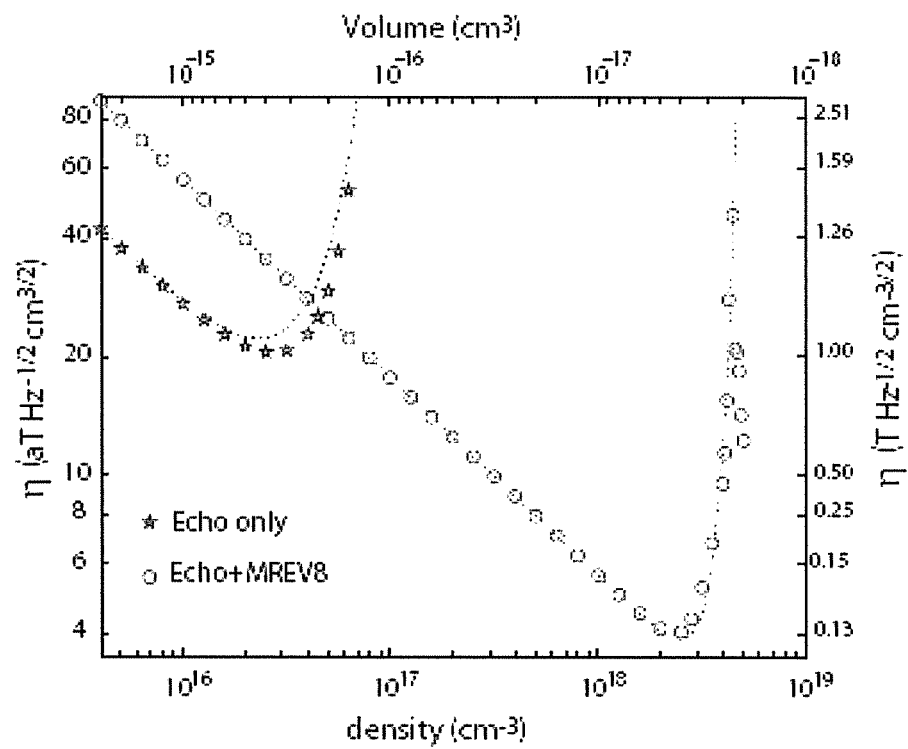
FIG. 8 is a graph of the simulated sensitivity as a function of NV center density, in an embodiment in which a solid state electronic spin system is used that includes a plurality of NV centers.

FIG. 8 illustrates the achievable sensitivity as a function of density, i.e. shows a graph of the simulated sensitivity as a function of NV center density, in an embodiment in which a solid state electronic spin system is used that includes a plurality of NV centers.

In FIG. 8, the simulated sensitivity in aT Hz$^{-1/2}$ cm$^{3/2}$ is shown as a function of NV center density, with dipolar interactions refocused by either a standard echo technique (plotted using stars) or a modified MREV8 sequence (plotted using circles). The simulation was performed for 10 spins. The decoupling sequence was repeated 3 times (102 pulses) with a $\tau$ spacing of $\approx 2$ μs and the π-pulse duration 50 ns. The magnetic field frequency was 10 kHz (close to the optimal frequency for $T_2$=250 μs and a 3-echo measurement) yielding a sensitivity as low as 4 aT Hz$^{-1/2}$ cm$^{3/2}$. The dotted lines indicate the analytical results from the moment expansion calculations.

To push the sensitivity limits beyond the cutoff imposed by spin-spin interactions and take advantage of the high NV center densities, ideas may be borrowed from dynamical decoupling, of which spin echo is an archetypal sequence. By applying external, time-dependent controls, this technique causes the system to evolve under an effective time-averaged Hamiltonian that is an appropriate symmetrization of the undesired interactions. For example, by using collective rotations, the interaction $H_{zz}$ can be successively rotated through the x, y and z axes for the same time duration, so that on average the spins will experience the Hamiltonian:

$$H_{iso} = \sum_{jk} \tilde{D}_{jk}(S_{j,x}S_{k,x} + S_{y,j}S_{k,y} + S_{j,z}S_{k,z})$$

Since this isotropic Heisenberg Hamiltonian commutes with the signal perturbation and the external magnetic field, assuming that the magnetic field is spatially homogeneous over the magnetometer volume, the Hamiltonian causes no harm to the spin evolution necessary for magnetometry. The control sequence also affects the spins interaction with the signal field, whose average is rotated and rescaled.

Embedding this control sequence within a spin echo sequence simultaneously transforms the dipolar interaction into the harmless isotropic interaction, while averaging to zero all time in-variant linear terms $\propto S_z$, as required to avoid the dephasing caused by nuclear spins and other paramagnetic impurities. Simple sequences perform the averaging only to first order in time but more complex concatenated sequences can achieve averaging of higher order terms. The convergence to the averaged interaction holds provided the pulse switching frequency is fast on the scale set by the internal couplings and the bath spectral density, a condition that is expected to be accessible experimentally.

Figure 9:
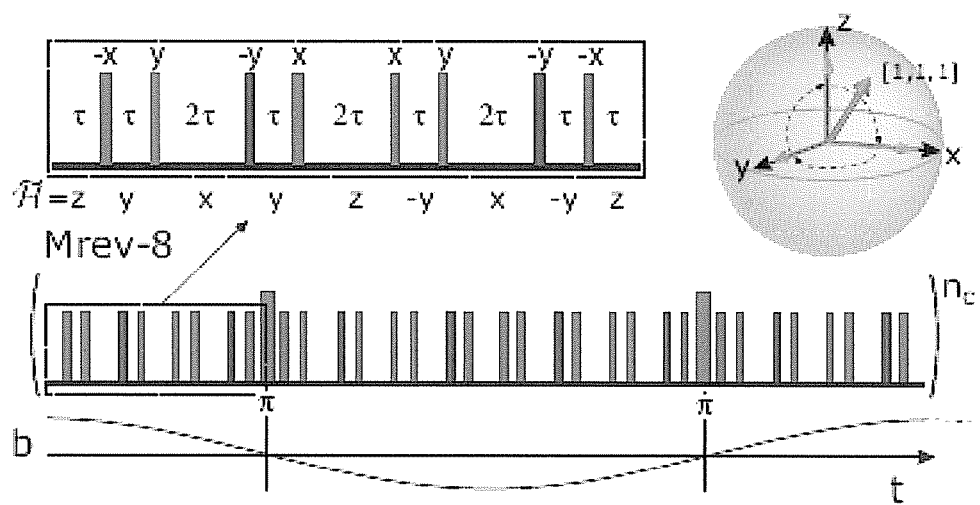
FIG. 9 illustrates a pulse sequence for dynamically decoupling unwanted interactions.

In one embodiment, an MREV8-type sequence may achieve these goals, as shown in FIG. 9. FIG. 9 illustrates a Ramsey-type pulse sequence for dynamically decoupling unwanted interactions. Dynamical decoupling of unwanted interactions may be obtained by coherent averaging. By means of an external control the internal Hamiltonian may be made time-dependent. Using cyclic MPS (multiple pulse sequences) and considering only stroboscopic measurements, the evolution may be described by an effective Hamiltonian that, to leading order in time, is given by the time average of the modulated internal Hamiltonian. Higher order terms in the effective Hamiltonian expansion, $H_{eff} = \overline{H}^{(1)} + \overline{H}^{(2)} + \ldots$, may also be calculated using average Hamiltonian theory and the MPS tailored to produce the desired evolution.

In the exemplary decoupling sequence shown in FIG. 9, the narrow bars are $\pi/2$ pulses around different axes in the $m_s = \pm 1$ manifold, while the wide bars are $\pi$-pulses. The overall pulse sequence illustrated in FIG. 9 is comprised of 34 pulses, with a cycle time of 48τ. The variable b in FIG. 9 stands for the AC field to be measured. During the total averaging interval T, T/τ measurements can be made, yielding a shot-noise-limited sensitivity η given by the minimum detectable field, $$b_{min} \equiv \eta / \sqrt{T} = \frac{\hbar}{g\mu_B} \frac{1}{\sqrt{T}} / \sqrt{T}.$$

Increasing the number of sensing spins results in further improvement of sensitivity.

In the inset in FIG. 9, the MREV8 sequence is shown, which comprises 8 pulses with cycle time 12τ. The z-component of the spin vector is cyclically rotated through the y, x and z direction so that the average spin vector is along the [1, 1, 1] axis, as in the sphere illustrated in FIG. 2. The $H_{zz}$ Hamiltonian becomes $\overline{H}_{zz}^{(1)} = H_{iso}/3$ and the linear Hamiltonian $S_z \to (S_z + S_x)/3$. $\hat{H}$, shown in the inset, is the direction of the internal Hamiltonian in the interaction frame.

By preparing the spins in a direction $\approx \pi/4$ in the z-x plane the accumulated phase is $\sqrt{2/3} \approx 0.47$ of that acquired during an echo sequence of equivalent duration and the most important error contribution from the residual dipolar Hamiltonian is a third order correction term. Thus the sensitivity improves to $$\eta_{AC}^V = \frac{\hbar}{g\mu_B} \frac{3\pi e^{(\tau/T_2)^3}}{C\sqrt{2n\tau}} e^{\tilde{\alpha} n^6 \tau^2}.$$

The coefficient $\tilde{\alpha}$ can be estimated to be of order $$\left(\frac{\mu_0}{4\pi} \frac{(g\mu_B)^2}{\hbar}\right)^6 \delta\tau^4,$$

where δτ is the interval between pulses and τ the total measurement time ($\propto 48\delta\tau$). In the embodiment shown in FIG. 9, the dynamics of a small number of spins (N=10) was simulated, under the influence of the modified MREV8 sequence as a function of spin density, taking into account the finite width of the pulses.

The improvement in sensitivity with respect to a simple echo measurement is clearly seen in FIG. 9: the sensitivity can be as low as 4 aT Hz$^{-1/2}$ cm$^{-3/2}$ at 10 kHz. By varying the number of cycles over which the signal is recorded, using concatenated decoupling sequences, it is possible to obtain similar sensitivities over a wide range of frequencies. The maximum frequency is constrained by the ability to perform fast ESR pulses while the minimum frequency is set by the $T_2$ time.

In the illustrated embodiment, the MREV8 sequence is chosen for its robustness against pulse errors. The linear term $S_z$ (and therefore the signal) is scaled by $\sqrt{2/3}$ and rotated to the z+x axis. A π-pulse in between two MREV8 sequences may cause any quasi-static term proportional to z to go to zero, while retaining the AC signal. Time symmetrization of the sequence may bring to zero the second order terms.

The dephasing function may then given by the leading order error $\overline{H}_{zz}^{(3)}$ (neglecting the second order correction given by the cross-terms of the external field and the dipolar Hamiltonian). Its effects may be captured by a moment expansion |° to second order of the effective Hamiltonian, $\langle D^6 \rangle = \text{Tr}[[\overline{H}_{zz}^{(3)}, J_\perp]/\text{Tr}[J_\perp^2]$, where $J_\perp = \Sigma_k S_{\perp,k}$ is the collective spin in a direction perpendicular to z. $\langle D^6 \rangle$ may have the character of a sixth moment and its value is a function of the sixth power of the local field generated by the dipolar interaction. The sensitivity decay rate is thus proportional to the sixth order of the density and the square of the total time, with a coefficient $$\tilde{\alpha} = D^6/n^6 \sim \left(\frac{\mu_0}{4\pi} \frac{(g\mu_B)^2}{\hbar}\right)^6 \tau^4.$$

The MREV8 sequence entails a large number of control pulses. For many typical errors, for example phase-lag and overshoot/undershoot, the refocusing may only be affected at higher order. However, depolarizing pulse errors occurring with probability p lead to a reduction of contrast: CC'=C(1−p)$^k$ for k pulses. Using the MREV8 sequence with echo gives k=34 and a requirement p≤0.0002 for contrasts near unity.

More complex detection techniques, such as multiple-pulse echo sequences embedded in the dipolar coupling refocusing sequence, may allow good sensitivity to be maintained at higher frequency signal fields, ranging from tens of kHz up to MHz. Furthermore, integration of a thin crystal of diamond with a CCD detector may allow for individual "pixel" elements, corresponding to individual pixels of the CCD. For a 10 μm thick crystal with (2 μm)² "pixels", each pixel could achieve 1 pT Hz$^{-1/2}$ sensitivity with a few micron spatial resolution of the signal field.

When the signal field is macroscopic, such as in low field MRI, larger diamond crystals may provide extremely sensitive detection. For example, in the detection of proton NMR (426 kHz in a 10 mT field), a 0.01 cm³ diamond with $10^{18}$ centers per cm⁻³ would provide a sensitivity η≈60 aT Hz$^{-1/2}$ for measurement in ambient conditions. This compares with η≈800 aT Hz$^{-1/2}$ for SQUIDS and η≈1-0.5 fT Hz$^{-1/2}$ for atomic magnetometers, while having a substantially smaller (by a factor of 10) detector volume.

Increasing even further the diamond volume could potentially lead to the detection of atto Tesla fields, opening the prospect of improved tests of fundamental symmetries and physical laws. The sensitivity could be also improved by working with synthesized, isotopically purified diamond containing lower fraction of C-13. Other paramagnetic centers in various materials may also be considered. Many potential applications of such nano-sized centers may be found in bio-science.

These considerations indicate that coherent control of electronic spins in diamond can be used to create a magnetic field sensor of unprecedented sensitivity and spatial resolution. Further refinements could include using non-classical spin states, such as squeezed states induced by the spin-spin coupling. Potential applications in bio-science, materials science, fundamental physics and single electron and nuclear spin detection can be foreseen.

High-field magnetometry is another regime of operation for a NV center-based magnetometer. In particular, for fields such that the Larmor precession of Carbon-13 is much faster than the hyperfine interaction with the electronic spins of the NV center, ESEEM (Electron Spin Echo Envelope Modulation) is also highly suppressed. Thus, for fields above ~100 mT, the NV system may be still be used for vector magnetometer with the 0-1 manifold.

In some embodiments, the effects of different NV center orientations may be considered. In order to use the NV centers as a vector magnetometer, the signal should originate only from one of the four different crystallographic axes (for example the (111) axis). Under application of a DC transverse magnetic field $B\perp \hat{x}$, the spectator centers (with crystalline axis $\hat{n}$ have the $|\pm 1\rangle$ levels split by $g\mu_B B\perp \hat{x}\cdot\hat{n}$. This detunes the other three classes of centers from the microwave field used for preparing and manipulating the $m_s=\pm 1$ subspace, with ideal choice of $\hat{x}$ aligned with the (½, ½, $\bar{1}$) axis. For pulse errors to be smaller than the assumed measurement errors for the desired (111) axis, it is required that $\Omega \leq 3\pi/T^*_2$. This translates to a requirement that $g\mu_B B\perp>3\hbar\Omega\sqrt{3/2}$ for the other three axes. For $T^*_2=1$ μs, it is required that $B\perp\geq 0.3$ mT.

In some embodiments of a NV center based magnetometry in accordance with the present disclosure, the four crystallographic classes of NV centers may be exploited to provide a full 3D vector and scalar magnetometer. This may be achieved by changing the direction of the biasing transverse field $B\perp$ in between measurements. By alternating between three crystalline axes, a full vector measurement of the signal is, in principle, possible. This may reduce the overall integration time for a given axis by a factor of three, as well as requiring additional calibration of the ESR field strengths and measurement efficiencies.

In the high density regime, the spectator centers may also cause unwanted couplings to the active NV centers. In general, the interaction between NV centers and any paramagnetic (epr) impurity reduces the signal by a multiplicative factor $$1-\varepsilon_{jk} = 1-2\frac{D^2_{jk,z}+D^2_{jk,y}}{|g\mu_B B\perp|^2}\approx \exp(-\varepsilon_{jk}),$$

provided a biasing field $g\mu_B B\perp \gg |\overline{D_{jk}}|$ is applied. For many randomly located impurities, the factor becomes $\exp(-\varepsilon_j)$ with $$\varepsilon_j = \sum_k \varepsilon_{jk} \approx \frac{(\mu_0 g\mu_B)^2 n_{epr}}{12\pi r_0^3 B_\perp^2},$$

where $r_0$ is the closest epr impurity spacing that does not detune the NV center off resonance ($r_0\approx 3$ nm) and $n_{epr}$ is the density of epr centers. As the bias field is increased in strength, the paramagnetic impurities get averaged by their fast rotation, leading to an improved signal for the NV center system. For $B\perp=0.3$ mT, $\epsilon\approx n_{epr}\times 5\times 10^{-33}$ cm³, which remains negligible even for $n_N>10^{19}$ cm⁻³.

In sum, the present disclosure provides methods and systems for enhancing the spatial resolution and magnetic field sensitivity of solid-state magnetometers based on electronic spin systems, such as defects in crystals and semiconductors. A particular example has been described of such a solid-state magnetometer system, namely NV-diamond, i.e. the electronic spins associated with Nitrogen vacancy centers in diamond.

Techniques described in the present disclosure include, but are not limited to: (i) coherent control schemes (e.g., using RF pulses) to decouple electronic spins from the local environment and from each other, leading to a substantial improvement in sensitivity to external time-varying magnetic fields and magnetometer operation at high spin densities; (ii) attaching a nano-sized crystal containing one or several spins (e.g., NV centers) to the tip of an atomic force microscope, optical fiber or plasmonic waveguide, to be used as a scanning magnetic probe capable of detecting localized sources of magnetic fields with nanoscale resolution; (iii) integration with super-resolution optical techniques such as STED, for combined far-field imaging and magnetometry with resolution better than the conventional diffraction limit; (iv) use of magnetic field gradients to improve spatial resolution to <1 nm by localizing the region of electronic spin resonance with the applied RF radiation; (v) operation as a vector magnetometer by use of spins in specific crystallographic classes and/or quantization axis; and (vi) use of the measured magnetometer signal variance as the magnetic field probe, e.g., when the magnetic field frequency and/or phase vary in time.

The extremely high magnetic field sensitivity in a small volume offered by solid state spin-qubits such as NV centers in diamond can find a wide range of applications, from fundamental physics tests or quantum computing applications to detection of NMR signals, surface physics and material science, structural biology, intracellular bioimaging, and medical imaging and biomagnetism. This robust technology could be invaluable both in nanoscale magnetic field imaging and in macroscopic field detection scenarios, such as low-field MRI and mapping dynamics of neural circuits.

The methods and systems described in the present disclosure would enable superior spatial resolution and magnetic field sensitivity to existing state-of-the-art techniques, including SQUIDs, atomic vapor-based magnetometers, and magnetic resonance force microscopy. Intended or possible future uses of such methods and systems include, but are not limited to the detection and mapping of AC and DC magnetic fields with high-spatial-resolution, as small as about 0.1 nm, and high-sensitivity, as low as about 1 atto tesla. Such detection and mapping may be performed in a robust, solid-state package that operates at ambient conditions, such as room temperature. The methods and systems described in the present disclosure may find wide applications in improved sensing, diagnostics and guidance of nano-scale manufacturing, for example in biology and medicine. Applications in biology and medicine may include, but are not limited to, structural biology, intracellular bioimaging, mapping neural activity and low-field NMR/MRI, semiconductors and electronics, materials analysis, and detection of rare isotopes, for example for homeland security.

One or more of the systems and methods described above may be implemented using a processing system, including but not limited to a control and data processing system. The methods in the present disclosure are not described with reference to any particular programming language. It will be appreciated that a variety of programming languages may be used to implement the teachings of the present disclosure. The system may be selectively configured and/or activated by a computer program stored in the computer.

Such a computer program may be stored in any computer readable storage medium, including but not limited to, any type of disk including floppy disks, optical disks, CD-ROMs, and magnetic-optical disks, ROMs (read-only memories), RAMs (random access memories), EPROMs (erasable programmable read-only memories), EEPROMs (electrically erasable programmable read-only memories), magnetic or optical cards, or any type of media suitable for storing electronic instructions.

The methods and systems presented herein are not inherently related to any particular computer, processor or other apparatus. Various general purpose systems may be used with different computer programs in accordance with the teachings herein. Any of the methods and systems described in the present disclosure may be implemented in hard-wired circuitry, by programming a general purpose processor, a graphics processor, or by any combination of hardware and software.

It is contemplated that the subject matter described herein may be embodied in many forms. Accordingly, the embodiments described in detail below are illustrative embodiments, and are not to be considered limitations. Other embodiments may be used in addition or instead.

The components, steps, features, objects, benefits and advantages that have been discussed are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages. The components and steps may also be arranged and ordered differently.

The phrase "means for" when used in a claim embraces the corresponding structures and materials that have been described and their equivalents. Similarly, the phrase "step for" when used in a claim embraces the corresponding acts that have been described and their equivalents. The absence of these phrases means that the claim is not limited to any of the corresponding structures, materials, or acts or to their equivalents.

Nothing that has been stated or illustrated is intended to cause a dedication of any component, step, feature, object, benefit, advantage, or equivalent to the public, regardless of whether it is recited in the claims.

In short, the scope of protection is limited solely by the claims that now follow. That scope is intended to be as broad as is reasonably consistent with the language that is used in the claims and to encompass all structural and functional equivalents.

What is claimed is:

1. A magnetometer for detecting and measuring a magnetic field, comprising:
    a source of RF radiation;
    an optical system configured to collect and transmit therethrough photons of optical radiation;
    a solid state diamond lattice adapted to be disposed in a magnetic field to be measured, the lattice comprising one or more nitrogen vacancy centers having one or more electronic spins, said lattice being responsive to said optical radiation and RF radiation;
    wherein the electronic spins are configured to undergo a Zeeman shift in energy level when disposed in a magnetic field, the Zeeman shift being proportional to magnetic field strength; and
    a detector configured to detect output optical radiation from the electronic spins of the diamond lattice, after they have been exposed to the optical and RF radiation, to measure the Zeeman shift from the output optical radiation so as to determine the magnetic field.

2. The magnetometer of claim 1, wherein the diamond lattice comprises one of:
    a nanocrystal; and
    a bulk diamond sample.

3. The magnetometer of claim 1, wherein the optical system comprises an optical waveguide, and wherein the sample is attached at the end of the optical waveguide.

4. The magnetometer of claim 1, further comprising an optical source configured to generate the optical radiation that causes the electronic spin to align along a direction.

5. The magnetometer of claim 4, wherein the optical source comprises a laser.

6. The magnetometer of claim 2, wherein the nanocrystal has a diameter between about 5 nanometers to about 50 nanometers, and wherein the sensitivity of the magnetometer is better than about 1 micro T $Hz^{-1/2}$.

7. The magnetometer of claim 1, wherein the sensitivity of the magnetometer is better than about 1 micro T $Hz^{-1/2}$.

8. A method of increasing the sensitivity of a magnetometer comprising:
    providing a magnetometer comprising a solid state diamond lattice, the lattice comprising one or more nitrogen vacancy centers having one or more electronic spins, said electronic spins being configured to undergo a Zeeman shift in energy level in the presence of a magnetic field, the Zeeman shift being proportional to the magnetic field strength,
    disposing the lattice in a magnetic field to be measured,
    applying photons of optical radiation,
    applying a sequence of RF pulses to dynamically decouple the electronic spins from mutual spin-spin interactions and from interactions with the lattice to increase the sensitivity of the magnetometer, and
    detecting output optical radiation from the electronic spins of the diamond lattice, after they have been exposed to the photons of optical radiation and RF pulses, to measure the Zeeman shift from the output optical radiation so as to determine the magnetic field.

9. The method of claim 8, wherein the magnetic field is aligned along an axis, and at least some of the RF pulses are configured to cause one or more of the electronic spins to rotate around the magnetic field.

10. The method of claim 8, wherein at least some of the RF pulses are configured to cause one or more of the electronic spins to transition to a different spin state.

11. The method of claim 9, wherein the sequence of RF pulses comprises at least one of:
a Hahn spin-echo sequence; and
a Carr Purcell Meiboom Gill sequence.

12. The method of claim 8, wherein the sequence of RF pulses comprises a MREV8 pulse sequence.

13. A method of detecting a magnetic field, comprising:
applying optical excitation radiation to a solid state electronic spin system disposed in a magnetic field to be measured that contains a plurality of electronic spins within a solid state diamond lattice, the lattice comprising one or more nitrogen vacancy centers having one or more electronic spins, thereby aligning the electronic spin with the magnetic field;
applying one or more pulses of RF radiation to the aligned electronic spins so as to induce a precession of the electronic spins about the magnetic field to be sensed, the frequency of the precession being linearly related to the magnetic field by the Zeeman shift of the electronic spin energy levels;
coherently controlling the electronic spins by applying a decoupling sequence of RF pulses so as to decouple the electronic spins from mutual spin-spin interactions and from interactions with the lattice; and
detecting output optical radiation from the solid state electronic spin system after the electronic spins have been subject to the optical excitation radiation and the RF radiation, to measure the Zeeman shift so as to determine the magnetic field.

14. The method of claim 13, wherein the sequence of RF pulses comprises at least one of:
a Hahn spin-echo sequence;
a Carr Purcell Meiboom Gill sequence; and
a MREV8 pulse sequence.

15. A vector magnetometer for detecting a magnetic field that is aligned with one of the crystallographic axes of a solid, the vector magnetometer comprising:
a macroscopic sample of the solid that includes a diamond crystal lattice the lattice comprising a relatively high density of nitrogen vacancy centers having one or more electronic spins,
an optical source configured to generate optical excitation radiation that causes the electronic spins to align with the magnetic field when the optical radiation is applied to the electronic spins;
an RF (radiofrequency) source configured to generate pulses of an RF field that induce a precession of the electronic spins about the magnetic field to be sensed, the frequency of the precession being linearly related to the magnetic field by the Zeeman shift of the electronic spin energy levels; and
a detector configured to detect output optical radiation from the solid state electronic spin system after the optical radiation from the optical source and the RF radiation from the RF source have been transmitted through the electronic spins;
wherein the RF source is further configured to apply the RF radiation only to electronic spins that are aligned along one or more predetermined crystallographic axes.

16. The vector magnetometer of claim 15, wherein the RF source is further configured to change the direction of the RF field in between one or more measurements performed by the magnetometer.

17. The vector magnetometer of claim 15, wherein the RF source is further configured to apply the RF radiation only to electronic spins that are aligned along predetermined quantization axes.

* * * * *

UNITED STATES PATENT AND TRADEMARK OFFICE
CERTIFICATE OF CORRECTION

PATENT NO. : 8,547,090 B2  Page 1 of 1
APPLICATION NO. : 12/746128
DATED : October 1, 2013
INVENTOR(S) : Lukin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 430 days.

Signed and Sealed this

Fifteenth Day of September, 2015

Michelle K. Lee
*Director of the United States Patent and Trademark Office*